United States Patent [19]

Cohen

[11] Patent Number: 4,794,533

[45] Date of Patent: Dec. 27, 1988

[54] SYSTEM ACTIVITY CHANGE INDICATOR

[75] Inventor: Daniel E. Cohen, Eden Prairie, Minn.

[73] Assignee: CNS, Inc., Eden Prairie, Minn.

[21] Appl. No.: 928,522

[22] Filed: Nov. 7, 1986

[51] Int. Cl.$^4$ .......................... G06F 15/42; A61B 5/00
[52] U.S. Cl. ............................... 364/413.05; 128/731; 324/77 A
[58] Field of Search ....................... 364/417, 483, 485; 128/731; 324/77 A

[56] References Cited

U.S. PATENT DOCUMENTS

| | | | |
|---|---|---|---|
| 3,760,796 | 9/1973 | Baessler et al. | 128/2.1 B |
| 4,214,591 | 7/1980 | Sato et al. | 128/731 |
| 4,254,779 | 3/1981 | Miyata et al. | 128/731 |
| 4,279,258 | 7/1981 | John | 128/731 |
| 4,412,547 | 11/1983 | Callahan et al. | 128/731 |
| 4,417,592 | 11/1983 | John | 128/731 |
| 4,579,125 | 4/1986 | Strobl et al. | 128/731 |
| 4,610,259 | 9/1986 | Cohen et al. | 128/731 |
| 4,670,711 | 6/1987 | Daniels | 364/518 |

OTHER PUBLICATIONS

Willison, R. G., "Analysis of Electrical Activity in Healthy and Dystrophic Muscle in Man", *J. Neurol. Neurosurg. Psychiat.*, 27, 1964, pp. 386–394.
Fitch, P. and Willison, R. G., "Automatic Measurement of the Human Electromyogram", *Proceedings of the Physiological Society*, 19–20, Feb. 1965, pp. 28–29.
Rose, A. L. and Willison, R. G. (1967), "Quantitative Electromyography Using Automatic Analysis: Studies in Healthy Subjects and Patients with Primary Muscle Disease", *J. Neurol. Neurosurg. Psychiat. (London)*, 30, pp. 403–410.
Fitch, P., "An Analyser for Use in Human Electromyography", *Electronic Engineering*, Apr. 1967, pp. 240–243.
Hayward, M. and Willison, R. G., "The Recognition of Myogenic and Neurogenic Lesions by Quantitative EMG", *New Developments in Electromyography and Clinical Neurophysiology*, Institute of Neurology, London, edited by J. E. Desmedt, vol. 2, pp. 448–453 (Karger, Basel 1973).

*Primary Examiner*—Jerry Smith
*Assistant Examiner*—Allen MacDonald
*Attorney, Agent, or Firm*—Kinney & Lange

[57] ABSTRACT

A system for measuring changes in the number of maxima and minima occurring in a signal over time which changes indicate activity changes in a subject from which the signal measured is obtained.

20 Claims, 3 Drawing Sheets

SYSTEM ACTIVITY CHANGE INDICATOR

BACKGROUND OF THE INVENTION

Field of the Invention

The present invention relates to the determination of activity changes occurring in a system in response to stimuli applied thereto or a task undertaken thereby, and more particularly, to changes in brain activity as represented in electroencephalographic signals in response to stimuli provided thereto.

In electroencephalography, minute electrical signals produced in the brain are monitored, analyzed and often recorded. The interpretation of such signals forms a basis for neurological research and for neurological clinical diagnosis.

The electroencephalograph measures the electrical potential at the surface of the scalp of the subject's head by the use of electrodes pasted to the surface of the scalp at one or more of the standard positions adopted by the International Federation of Electroencephalography in what is called the 10/20 system. Typically, when used for a diagnosis, there may be as many as 20 electrodes provided in this manner which are connected to encephalographic equipment to provide indications of the potentials measured. These potentials are typically in the range of 1 to 100 $\mu$v. These potentials can be spontaneous but are often measured in connection with the occurrance of some sort of brain stimulator controlled by the electroencephalographic equipment, such as a shifting light pattern to be perceived by the subject's eyes.

These electroencephalographic (EEG) signals, or measured potentials, have differing frequency content depending upon activities in the biological system including the brain. This frequency content has come to be classified into four basic frequency bands as follows: the "delta" band, 0 to less than 4 Hz; the "theta" band, 4 to less than 8 Hz; the "alpha" band, 8 to less than 13 Hz; and the "beta" band, greater than 13 Hz. A typical kind of information desired to be acquired from the EEG signals during a particular time period is the predominant frequency in a particular signal during that period. Determining this requires considerable training and is highly dependent on the skill of the neurologist, since an EEG signal portion typically includes many frequency components.

This analysis can be made more convenient and even improved by the use of signal processing equipment to provide parameters and characteristics of the data obtained in such EEG signals. For instance, providing one or more EEG signals to a computer properly programmed permits performing an analysis of the frequency spectrum contained in such signal or signals.

In such an arrangement, the EEG signal which is, of course, an analog signal, is sampled in amplitude over a selected interval of time with each such sample converted to its digital value and stored, at least temporarily, in the computer. These consecutive digitized samples, consecutive in the time order they are obtained from the sampled signal, are transformed from the time domain to the frequency domain by means of some fast Fourier transform (FFT) algorithm. The results of the transformation represent a frequency spectrum showing the frequency content in the signal sample measured. Such a spectrum can be displayed as a graph with the amplitude of the frequency components contained in the signal presented along a frequency axis.

Discrete Fourier transforms are defined for such digitized samples for which FFT algorithms can be used because such arrangements provide the corresponding frequency spectrum relatively quickly by reducing the amount of computation required. The samples could be acquired and ordinary Fourier methods used to obtain a frequency spectrum, but this would be a complex and time-consuming arrangement. Nevertheless, this latter arrangement has one virtue in that the interval over which the signal is acquired and sampled does not affect the outcome. In using the former arrangement to speed the conversion to the frequency domain, however, a limitation on the minimum amount of time in which data must be acquired is introduced because the length of that interval determines the period of the lowest frequency in the frequency spectrum resulting from use of such methods.

Because EEG signals contain very low frequencies in them which are of great interest to the neurologist, the intervals for acquiring data must be quite long if such frequencies are to be obtained. If shorter time intervals for obtaining data were used, the lowest frequency which could be contained in the spectrum would be a larger frequency value and information of interest would be lost. For example, a time interval of 1 second means that frequencies as low as about 1 Hz could be presented, but a data acquisition of 20· millisecond would result in the lowest frequency being presented being about 50 Hz.

This frequency domain representation problem is a significant problem because the changes in activity in a biological system in response to a stimulus will occur in time durations considerably less than one second, but frequency content in signals representing such changes will contain frequencies of interest in the range of 1 Hz. Thus, a desirable arrangement would show system activity changes occurring in reasonable fractions of a second after a stimulus including aspects of interest in such changes as contained in signals representing information with respect to these changes having frequency components of a period longer than the duration required for the changes to occur.

SUMMARY OF THE INVENTION

The present invention provides a means for acquiring samples of signals representing activity in a system that is either spontaneous or in response to a stimulus, and a signal processing means for receiving these samples and finding the relative magnitude relationship between each sample and its neighbors as a basis for indicating the occurance of changes in the system activities signals. The numbers of these changes occurring over successive fractional portions of the data acquisition period give an indication of the amount of change occurring in time over data acquisition period. If there are repeated system signals available for the same situation, these changes in activity at each point in time can be averaged to provide a more reliable activity indication at each point in time. The various results obtained can be made available to the user in any display arrangement found convenient for the purpose.

DETAILED DESCRIPTION OF THE PREFERRED EMBODIMENTS

Figure 1:
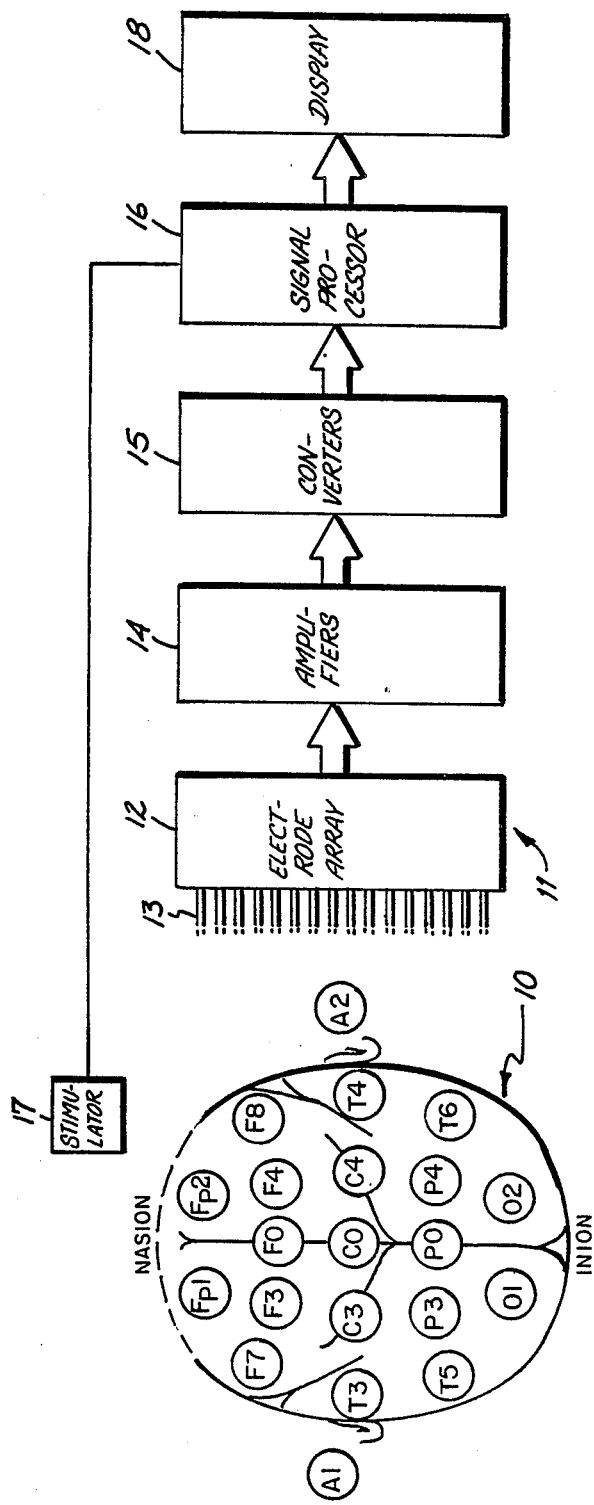
FIG. 1 is a diagram of the top of a typical human head and a block diagram along the signal path in the electroencephalographic signal analyzer of the present invention.

FIG. 1 shows the top of a subject's head, 10, and the standard positions on the scalp thereof for locating electrodes for electroencephalographic testing. The locations for the electrodes are identified by the commonly used designations Fp1, Fp2, F0, F3, F4, F7, F8, T3, T4, T5, T6, C0, C3, C4, P0, P3, P4, O1 and O2. Also shown are reference electrode locations A1 and A2 for the attachment of reference electrodes, these being commonly attached to one or both of the subject's ears.

To the right of head 10 in FIG. 1 is an electroencephalographic signal analyzing system, 11. Analyzer system 11 has an electroencephalographic electrode array module, 12, which has extending therefrom, though arbitrarily shortened in FIG. 1 to avoid obscurance, coupling cables, 13. Typically, there are sixteen electrodes for acquiring signals with one each provided on the far end of each one of coupling cables 13. A further electrode is on one of cables 13 for attachment as a reference, typcally to an ear but other connection possibilities exist and are frequently used. The electrodes need not be shown in FIG. 1 because they are well known pieces of standard equipment available for use with electroencephalographic testing systems. The electrodes not shown are intended to be placed at one of the designated locations shown on head 10. Depending on the nature of the test, there may be fewer than sixteen electrodes used in gathering data in any one test, but there may also be more.

The signals obtained by electrode array 12 are transmitted to an amplifying system, 14, which contains one amplifier for each of cables 13. Typically, each of these amplifiers is a differential amplifier and measures the signal transmitted by its corresponding coupling cable 13 with respect to the further cable used as a reference level attached at one or both locations A1 and A2 on head 10. These amplifiers provide a gain on the order of seventy thousand and can amplify signals containing frequencies up to several tens of Hz without degradation because of any frequency response limits of the amplifier. Such amplifiers need not be further described, as they are well known for use in electroencephalographic testing.

The amplified electroencephalographic analog signals are provided from amplification module 14 to an analog multiplexer and then to an anlog-to-digital converter contained in a conversion module, 15. Consecutive samples of the amplitude of each electrode acquired signal are taken consecutively, each during a selected time interval, and a digital value provided therefor in conversion module 15 in a well known manner. Conversion module 15 has been found to provide adequate resolution for the present state of the art if an analog sample is converted to a digital representation as a binary number of 14 magnitude bits and a sign bit.

As is well known, the taking of samples is repeated at fixed intervals at a rate or frequency which must exceed twice the highest frequency in the electroencephalographic signal which is to be represented by the samples. Thus, if the upper frequency content is uncertain, sampling rates should be increased accordingly to the point where there is no longer any concern about having exceeded twice the highest rate signal. A typical sampling rate for module 15 in this light would be 256 Hz, adequate for the present state of the art. Converters capable of the performance described in this paragraph are well known and readily available, and so require no further description here.

The digitized samples obtained in conversion module 15 are provided to a signal processing means, 16. Digitized samples for each of the signals obtained from a scalp location on head 10 are there analyzed to determine the changes in activity occurring therein in response to a stimulus provided to head 10 by a stimulus source, 17, under control of signal processing source 16. The results are provided to a display module, 18, where they can be presented to an operator.

Figure 2:
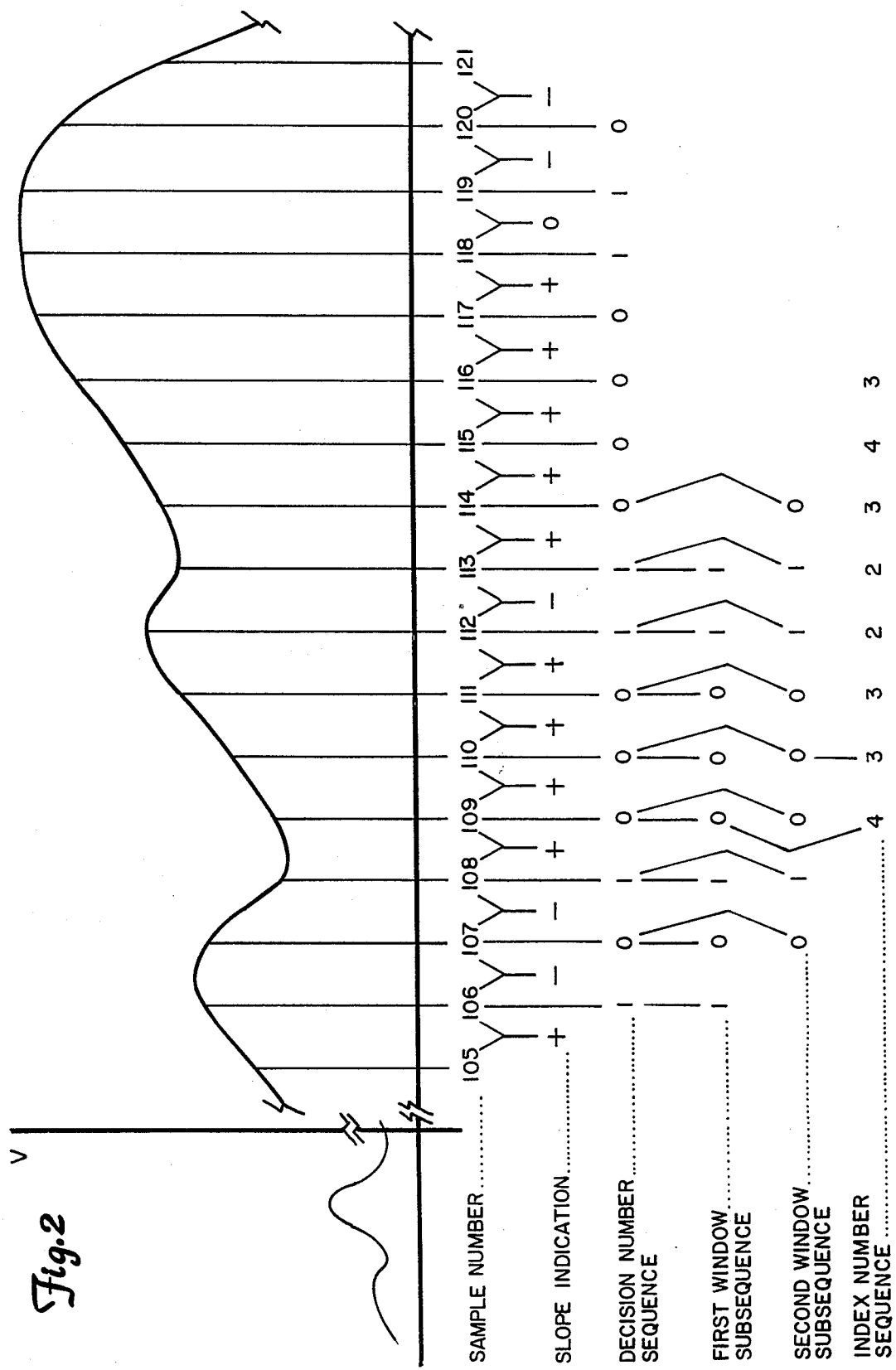
FIG. 2 is a portion of a typical waveform of an electroencephalographic signal with results of certain acquisition and signal processing steps shown therebelow.

A portion of a typical enecephalographic waveform transmitted by one of cables 13 gathering data is shown in FIG. 2 where the origin along a time axis represents the point of the application of the stimulus. The potential measured in the signal is plotted on the vertical axis as a voltage, v. Thin vertical lines intersecting the waveform are drawn from the waveform across the time axis down to a number which represents the number of the sample taken for that point of the waveform portion shown.

Note that breaks in both the time axis and the voltage axis are indicated near the origin so that this represents just a particular portion of waveform example chosen for illustration. That is, there is no significance in having chosen samples 105 through 121 to show, other than that these are typical. The entire waveform would be acquired over an interval typically of several tenths of a second to two seconds. The actual digitized values for samples 105 through 121 are not given or shown in FIG. 2, as this is unnecessary for purposes of explanation.

The activity changes represented in the electroencephalographic signal waveforms, which waveforms tend to be of the nature of a low frequency content broad wave with numerous higher frequency content superimposed waves occurring therealong, is represented primarily by increases and decreases in the number of superimposed wave peaks in different time segments over the waveform interval. That is to say, increases and decreases in the numbers of local minima and maxima in short time windows along the time axis are indicative of the activity changes of interest in the biological system of the brain which are either spontaneous or in response to stimuli applied thereto. Such activity changes are thought to be related to the cortical processing of information. Thus, measuring the numbers of maxima and minima occurring in short time segments about each point of time along the time axis is of great interest.

The changes in numbers of local maxima and minima come at frequencies significantly lower than the frequency contents of the superimposed wave peaks themselves. However, as earlier described, use of a frequency domain representation for very short periods of time as an indication of the number of changes occurring in the signal in the short window along the axis is not possible because the frequency lower limit to be represented by use of the FFT algorithm will be above the frequency content of the rate of change of the numbers of superimposed waveform peaks. Thus, checking the activity content in, for instance, a 20 millisecond window along the time axis will not provide any meaningful information if whatever is measured in this window is subjected to an FFT algorithm and the results displayed.

FIG. 2 shows a much better alternative based on finding the nature of the slopes of the waveform portions closely about each sample point and counting the inflection points where the slopes differ on either side of the samples taken during the data acquisition interval. This can be accomplished on the basis of the digitized samples in signal processing module 16 by considering each digitized sample with respect to its immediately neighboring digitized sample on either side thereof in the sequence of consecutive digitized amplitude samples obtained from conversion module 15.

Each sample, possible excepting the first and last samples in this sequence or alternatively substituting an arbitrary result therefor, has its amplitude value compared with the digitized sample on either side of it, that is, the sample occurring before and the one occurring after. Each such digitized sample will have a relative magnitude relationship with these two neighboring digitized samples, being either greater than, less than or equal to the value of the neighboring samples.

If the central digitized sample in this triplet is greater in magnitude than the preceding sample, the waveform between them is taken as having a positive slope and marked with a plus sign in the slope indication row beneath the sample number row in FIG. 2. If the central digitized sample has a lower value than the preceding one, there has been a negative slope. If the central digitized sample is of the same value there has been a zero slope.

Similarly, if the central digitized sample has had a magnitude greater than the following neighboring digitized sample, it is assumed the waveform between them has a negative slope. If the magnitude of the central digitized sample is less than that of the following neighboring sample, there has been a positive slope. Again, if they are equal there has been a zero slope in the waveform.

The result is that a positive slope, represented by a plus symbol, a negative slope, represented by a minus symbol, or a zero slope, represented by a zero, can be established for each consecutive pair of digitized samples in the sequence of digitized samples acquired over the acquisition interval in which the electroencephalographic signal is measured. This sequence of symbols is shown in the slope indication row in FIG. 2 for the example waveform given there.

A local minima or maxima, or inflection point, is taken to have occurred wherever in the slope indication row there is a change in symbol type in going along that row in FIG. 2. That is wherever there is such a change in the relative magnitude relationship between a central digitized sample and its immediately before and after neighboring samples, there is an indication that an inflection point has occurred. The number 1 is assigned as a decision number to each change in succeeding symbol type occurring along this slope indication row, and the number 0 is assigned as the decision number if there has been no change in symbol type in succeeding symbols in this row. The resulting sequence of relative magnitude decision numbers is shown in the decision number sequence row in FIG. 2.

With this decision number sequence established, a measure of change in numbers of local minima and maxima can be made about each point along the time axis in FIG. 2. This measure is based on defining a time window about that point and determining the number of maxima and minima occurring in that window. Then, the window is moved to the same relation about the next sample point and the minima and maxima are counted in that window as an indication of activity occurring at that subsequent sample point.

This may be done based on the decision number sequence by selecting a subsequence from the decision number sequence which contains therein the decision number at the data point for which an activity indication is to be given. While this subsequence would often be chosen to be centered about the associated decision number at the data point for which an activity indication is to be given, this need not necessarily be so. In FIG. 2, the first window subsequence is chosen so that there are three subsequence entries to the left of the decision number corresonding to the digitized sample for which an activity change measure is to be given, and four subsequence numbers to the right. This is because a window of eight decision numbers has been chosen as the window size over which an activity measure is to be formed.

The span of the time window chosen is a compromise between (i) being too large, and therefore averaging out the activity change differences at different points along the time axis, or in effect not giving sufficient resolution, and (ii) being too small so there is too much random change in the result due to other uncontrollable events occurring in the system. A typical window size in electroencephalography would be from 20 to 50 millisecond, which is approximately what is shown in FIG. 2 (actually 31 millisecond for a sampling rate of 256 Hz).

The first window sequence is extracted from the decision number sequence and repeated in a separate row in FIG. 2. This first window subsequence is for forming the activity measure to be presented in connection with sample point 109. This subsequence is related to the corresponding decision number sequence row portion by thin vertical lines therebetween. A second window subsequence for providing an activity measure for sample point 110 is shown as a second window subsequence row in FIG. 2. An angled thin line is shown between members of the second window subsequence and the corresponding decision numbers in the decision number sequence which they represent. This second window subsequence starts at one sequence number further along the decision number sequence than the first window subsequence, and finishes one number further along.

Similarly, window subsequences can be formed for each of the sample points in the sample sequence from the corresponding decision number sequence. Only first window and second window subsequences have been extracted and shown separately in FIG. 2.

The window, in form of a subsequence having been selected along the time axis within which a measure of system activity change is to be considered in determining the system activity change occurring about the sample point associated with that window, then has the measure of system activity change formed from the decision numbers contained therein. The subsequence has an arithmetic combination taken of the decision numbers therein to give the activity change measure.

This can be simply a summation of the decision numbers occurring in the subsequence which then gives a count of the local maxima and minima occurring in that span about the corresponding decision number and sample number as measured by the decision numbers. The first window subsequence using this measure of activity gives a value 4 which is shown in the last line in FIG. 2 as the first entry in the index number sequence. This index number is written below the decision number and the sample number to which it corresponds.

The second window subsequence gives a value of 3 using this measure, and is also shown in the index number sequence row in FIG. 2 below its corresponding decision number and sample number. Further entries in the index number sequence row are shown in FIG. 2 for each of the subsequent subsequences which are found for successive decision numbers in the decision number sequence in the manner as described for the first and second window subsequences.

This sequence of index numbers then provides a measure of the system activity changes occurring in the window about the sample to which the index number corresponds. Thus, a display of the index number sequence versus time provides a measure of the system activity changes occurring during the time in which data samples have been acquired after a stimulus is applied to the brain of the subject. The display, which could be provided on a video monitor or a recorder of a convenient sort, gives the user of the analyzer system a clear measure of system activity changes in response to a stimulus applied to the system without the user being required to do a great deal of interpretation to obtain such information.

The index number sequence could be formed in alternative ways if the user desires, based on a judgment that a different arithmetic combination of the decision numbers in a subsequence is more pertinent to the needs of the test determining system activity changes in response to a stimulus. For instance, a weighting function could be applied which would give different emphasis to some of the numbers in the decision number subsequences than to others. Thus, a window could be provided within the subsequence windows which was not uniform but which rather gave a different emphasis to some members of the subsequence than to others, depending on their positions according to some secondary window formulation. A typical one would be a Blackman window function following a cosine to the fourth power law which would give full weight to decision numbers in the subsequence close to the decision number which corresponds to the sample point for which the activity measure is being generated but gives relatively little weight to those decision numbers at the extremes of the subsequence.

Because of the complexity of the human brain, there are a number of other concurrent contributors to activity changes in response to a stimulus which are not necessarily related to that stimulus. Therefore, quite commonly the test of a subject's response to a stimulus will be repeated many times, perhaps as many as twenty-five to one hundred times. For each such test, a new index number sequence can be generated based on the same sampling rate over the same intervals taken with respect to the same stimuli at the same time reference. As a result, each of the corresponding index numbers in the results of each of the tests can be averaged in a further arithmetical combination. Thereby, there is provided a resulting measure of the system activity changes which has much of the variability due to other factors cancelled through the averaging process and with the activity changes due primarily to the stimuli being reinforced by the same averaging process. This result can then be displayed in the manner described above for a single test index number sequence.

A typical purpose for such testing in a clinical setting would be to determine whether changes in a brain's response to a stimulus have occurred because of injury or a disease, such as Alzheimer's disease. Thus, a stimulus can be chosen that is konwn to affect two portions of the brain and measurements are taken on each for a control group showing a certain duration of time elapsing between activity changes in one portion and those in another in response to the stimulus. Then, a subject suspected of having a deteriorated brain function can be measured with respect to the same stimuli and the elapsed time noted between activity changes occurring in that subject in simiar portions of the brain. A significant elapsed time difference between activity changes in the two portions of the brain of the subject as opposed to those in the healthy control group will tend to confirm deterioration.

Figure 3:
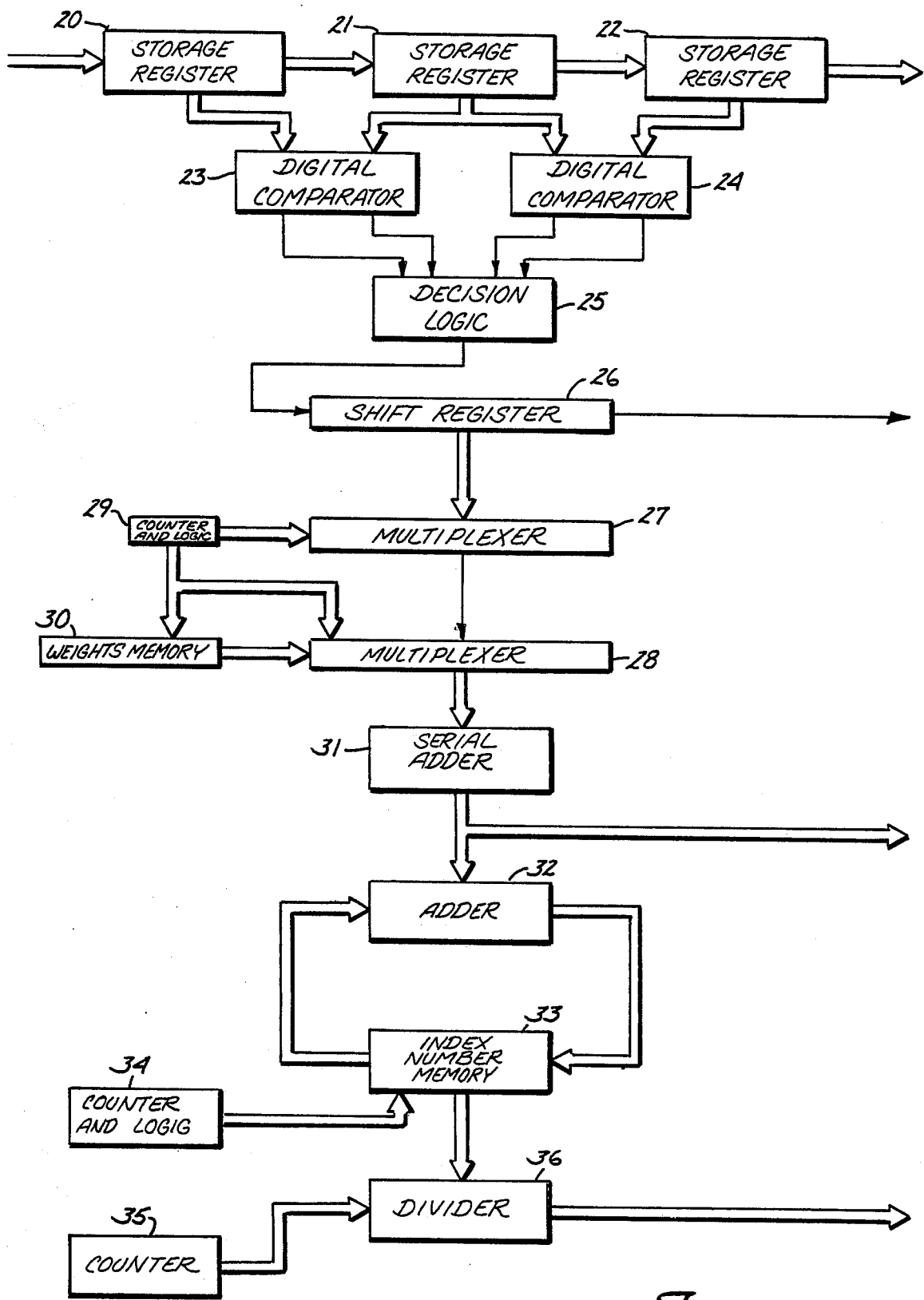
FIG. 3 is a block diagram showing somewhat greater detail for a block in FIG. 1.

Signal processing module 16 can be a general purpose computer used in a laboratory for research, or it could be a microprocessor in an analyzer unit in a smaller clinical setting. However, in some settings, a digital system dedicated to performing the functions just described may be desirable. A system of that nature for signal processing module 16 is shown in FIG. 3. FIG. 3 shows a special purpose system for operating on the digitized samples obtained from a single signal. For the multiple signals provided from module 12, the digital system of FIG. 3 could be repeated for each signal source or it could be used to operate on all of the signals through a multiplexing scheme. Timing and control circuitry have been omitted to clarify the presentation, but would be clear to one skilled in the art.

Digitized samples are provided from converter module 15 to a first register 20, where each is stored for one sample period. In the next sample period, the digitized sample stored in register 20 in the previous period is transmitted to, and stored in, another storage register, 21, and a new digitized sample is entered in register 20. Similarly, the digitized sample that had been stored in register 21 is transmitted to, and stored in, a further storage register, 22. The contents of register 22 can be discarded or, as shown in FIG. 3 further transmitted to a memory means if desired. In each sampling period, the digitized samples stored in registers 20 and 21 are presented to a digital comparator, 23. The digitized samples stored in registers 21 and 22 are presented to a second digital comparator, 24.

Comparators 23 and 24 each determine the above-described relative magnitude relationships between the digitized sample stored in register 21 and the digitized sample stored in registers 20 and 22, respectively. The results of these comparisons, whether the digitized sample in register 21 is greater than, less than, or equal to the digitized samples in the registers on either side thereof, are provided to a decision logic module, 25. Logic module 25 determines whether a 1 or a 0, denoting whether or not such relative magnitude relationships have changed, will be provided at its output as the next entry in the decision number sequence shown in FIG. 2. Thus, comparators 23 and 24 provide the relative magnitude decisions necessary for determining, in effect, whether a positive, negative or a zero slope indication is indicated between consecutive adjacent pairs of digitized samples with logic module 25 operating on those relative magnitude decisions to determine the decision number sequence.

The output of register 25 is entered into a shift register, 26, which has as many shift positions therein as are desired for a subsequence in effect forming a window along the time axis. Thus, for the situation described in FIG. 2, there would be eight shift positions in shift register 26. With each new sample period, a new value would be obtained from logic module 25 and shifted into the left-hand side of shift register 26 and the last value on the right-hand side would be shifted out. This last value could be discarded if unneeded or, as shown in FIG. 3, transmitted to some memory means if the decision number sequence is to be retained. Thus, shift register 26 always has in it a subsequence for a window such as the first window subsequence shown in FIG. 2. In the succeeding sampling period, the second window subsequence would appear in shift register 26. Similarly, in further succeeding sample periods, further window subsequences would appear in shift register 26.

Shift register 26 also has a parallel output to a multiplexer, 27. Multiplexer 27 selects in succession each storage site output from shift register 26 to be provided to a multiplexer, 28. Multiplexer 27 is driven by a counter and logic means, 29, which is reset at the beginning of each sampling period.

Multiplier 28 receives each decision number in a subsequence and multiplies it by a second window weighting function represented by weight values stored in a weight memory, 30. These weight values may be those calculated to provide the Blackman window as illustrated above. Of course, if no secondary window is to be used, then weight memory 30 and multiplier 28 can be eliminated.

The weighted subsequence members are then transmitted to a serial adder, 31, which receives all of the subsequence members and provides a total thereof once in each sampling period to form the index number corresponding to that sampling period, i.e. to the sample taken in that period.

Because repeated experiments are likely to be used, provision is made for transmitting the index number generated in serial adder 31 to a further adding and memory arrangement which includes an adder, 32, and an index number storage memory, 33. Also, as shown in FIG. 3, the index numbers from any one experiment could be stored separately, as suggested by the arrow pointing from the output of serial adder 31 to the right.

Adder 32 receives each index number from serial adder 31 and calls from memory 33 the total of all of the corresponding index numbers from earlier experiments stored in memory 33 then combines them and sends the result back to memory 33. A counter, and logic means 34, which is reset for each sampling period, supplies the proper addresses for memory 33. A further counter, 35, keeps count of the number of experiments and supplies this count to a divider, 36, which divides the number of experiments into the total for each index number position kept in memory 33 at the end of the experiments based on the repeated use of the stimuli to perform one set of experiments. These results then are supplied by divider 36 as the output of module 16 as shown by the arrow pointing to the right thereof. This output from module 16 is transmitted to display module 18 shown in FIG. 1, which may be a video terminal.

Many other implementations could be provided in place of that shown in FIG. 3 to accomplish the same end. Also, as earlier indicated, a digital computer could be programmed to perform the operations performed by the described digital system of FIG. 3. The programs required to have such computers perform the steps necessary to generate the decision number sequences and the index number sequences and the average of the index number sequences are straightforwardly accomplished by skilled computer programmers. Thus, although the present invention has been described with reference to preferred embodiments, workers skilled in the art will recognize that changes may be made in form and detail without departing from the spirit and scope of the invention.

What is claimed is:

1. A method for determining activity changes occurring in a system as these activity changes are represented in at least one signal representing system activity, said method comprising:
   acquiring a first sequence of consecutive samples of amplitude values of said system activity signal taken at a rate sufficient to represent those portions of said system activity signal related to said activity changes, said samples in said first sequence being acquired over a selected duration of time established with respect to a selected point in time;
   determining which relative magnitude relationship occurs from among first, second and third relative magnitude relationships between each sample in said first sequence and its immediately neighboring samples on either side thereof excepting those samples occurring first and last in said first sequence;
   forming a second sequence of decision numbers with each such decision number therein having a one-to-one correspondence with a said sample in said first sequence excepting those samples occurring first and last in said first sequence, each said decision number having one of a first selected set of values if its said corresponding sample in said first sequence has relative magnitude relationships with each of its immediately neighboring samples on either side thereof which are identical, but having one of a second selected set of values if its corresponding sample in said first sequence has relative magnitude relationships with each of its immediately neighboring samples on either side thereof which differ; and
   providing an indication of said activity changes based on said decision numbers.

2. The apparatus of claim 1 wherein said system activity signal is an electroencephalographic signal.

3. The method of claim 1 wherein said forming of a second sequence is followed by forming a third sequence of index numbers with each such index number corresponding to a said decision number in said second sequence, each said index number having a value equal to a selected first arithmetical combination of those decision numbers in a selected subsequence of decision numbers which include that decision number to which that said index number corresponds, and providing an indication of said activity changes based on said index numbers.

4. The method of claim 3 wherein said selected subsequence of decision numbers is formed of consecutive decision numbers with approximately an equal number of decision numbers therein on either side of said decision number to which said index number corresponds.

5. The method of claim 4 wherein selected ones of those decision numbers in said selected subsequence thereof have those values established therefor in forming said second sequence reduced before forming said selected first arithmetical combination of said decision numbers to form an index number with those said selected ones of such decision numbers farther from said decision number corresponding to said index number being reduced more.

6. The method of claim 5 wherein those steps of said acquiring of a first sequence, said determining of relative magnitude relationships, said forming of a second sequence, and said forming of a third sequence are initial steps and are repeated with respect to said system at a selected point in time to form a first set of repeat steps which are followed by forming a selected second arithmetical combination of each said index number in said initial steps with its corresponding index number in said first set of repeat steps, and providing an indication of said activity changes based on said selected second arithmetical combination.

7. The method of claim 3 wherein selected ones of those decision numbers in said selected subsequence thereof have those values established therefor in forming said second sequence changed before forming said first selected arithmetical combination of said decision numbers to form an index number.

8. The method of claim 3 wherein those steps of said acquiring of a first sequence, said determining of relative magnitude relationships, said forming of a second sequence, and said forming of a third sequence are initial steps and are repeated with respect to said system at a selected point in time to form a first set of repeat steps which are followed by forming a selected second arithmetical combination of each said index number in said initial steps with its corresponding index number in said first set of repeat steps, and providing an indication of said activity changes based on said selected second arithmetical combination.

9. The apparatus of claim 3 wherein said system activity signal is an electroencephalographic signal.

10. A detection system for determining activity changes occurring in a subject system as these activity changes are represented in at least one signal representing subject system activity, said detection system comprising:
   a signal acquiring means for acquiring said system activity signal;
   an analog-to-digital converter means for providing a first sequence of consecutive digitized samples of amplitude values of said system activity signal;
   a signal processing means for forming a second sequence of decision numbers with each such decision number therein having a one-to-one correspondence with a said sample in said first sequence excepting those samples occurring first and last in said first sequence, each said decision number having one of a first selected set of values if its said corresponding sample in said first sequence has relative magnitude relationships with each of its immediately neighboring samples on either side thereof which are identical, but having one of a second selected set of values if its corresponding sample in said first sequence has relative magnitude relationships with each of its immediately neighboring samples on either side thereof which differ; and
   a display means for providing an indication of said activity changes based on said decision numbers.

11. The system of claim 10 wherein said system activity signal is an electroencephalographic signal.

12. The system of claim 10 wherein said signal processing means if further capable of forming a third sequence of index numbers with each such index number corresponding to a decision number in said second sequence, each said index number having a value equal to a selected arithmetical combination of those decision numbers in a selected subsequence of decision numbers which include that decision number to which that said index number corresponds, and said display means provides an indication of said activity changes based on said index numbers.

13. The system of claim 12 wherein said signal processing means comprises a first, a second and a third register, each for storing a said digitized sample, said first register receiving consecutively and storing temporarily therein each said digitized sample provided by said analog-to-digital converter means and transferring to said second register for temporary storage therein that digitized sample immediately preceding each said digitized sample currently between received thereby, said second register receiving consecutively and storing temporarily therein said digitized samples transferred from said first register and transferring to said third register for temporary storage therein that digitized sample immediately preceding each said digitized sample currently being received thereby, said third register receiving consecutively and storing temporarily therein said digitized samples transferred from said second register, and wherein said system further comprises first and second comparator means each for comparing values of said digitized samples provided thereto and providing signals at an output thereof indicating whether one of those digitized samples has a value which is greater than, less than or equal to that of that other one provided thereto, said first comparator means being connected to said first and second registers to receive representations of those said digitized samples currently being stored in each for comparison, said second comparator means being connected to said second and third registers to receive representations of those said digitized samples currently being stored in each for comparison, and wherein said signal processing means further comprises a logic means for determining whether signals provided thereto are identical or differ and of providing signals at an output thereof indicating which condition is currently occurring, said logic means being electrically connected to said outputs of each of said first and second comparator means, and wherein said signal processing means further contains a first shift register means for receiving current signal portions at an input thereof for temporary storage therein and shifting each such signal portion along storage sites therein as each successive current signal portion is received at said input with said first shift register means input being electrically connected to said logic means output, each of said storage sites having a storage site output to which it is connected.

14. The system of claim 13 wherein said system further comprises a subsequence selector means connected to each of said storage site outputs and for receiving and storing temporarily said signal portions and making them available at least at one output thereof, and wherein said system further comprises an arithmetical combining means for performing arithmetic operations on signal portions provided thereto at at least one input thereof, said arithmetical combining means input being electrically connected to said subsequences selector means output.

15. The system of claim 10 wherein said signal processing means comprises a computer means.

16. The system of claim 15 wherein said signal processing means comprises a memory means for storing, at least temporarily, said digitized samples provided by said analog-to-digital converter means, a comparator means for comparing values of selected ones of said digitized samples stored in said memory means and of providing indications of which of selected digitized samples compared have values greater than, less than or equal to that selected other to which it is compared, logic means for providing indications of which of selected said indications provided by said comparator means are identical to or differ from other selected said indications provided by said comparator means, and a storage means for storing, at least temporarily, selected said indications of said logic means.

17. The system of claim 10 wherein said signal processing means comprises a memory means for storing, at least temporarily, said digitized samples provided by said analog-to-digital converter means, a comparator means for comparing values of selected ones of said digitized samples stored in said memory means and of providing indications of which of said selected digitized samples compared have values greater than, less than or equal to those values of selected others of said digitized samples stored in said memory means to which it is compared, logic means for providing indications of which of selected said indications provided by said comparator means are identical to or differ from other selected said indications provided by said comparator means, and a storage means for storing, at least temporarily, selected said indications of said logic means.

18. The system of claim 17 wherein said signal processing means comprises a first, a second and a third register, each for storing a said digitized sample, said first register receiving consecutively and storing temporarily therein each said digitized sample provided by said analog-to-digital converter means and transferring to said second register for temporary storage therein that digitized sample immediately preceding each said digitized sample currently being received thereby, said second register receiving consecutively and storing temporarily therein said digitized samples transferred from said first register and transferring to said third register for temporary storage therein that digitized sample immediately preceding each said digitized sample currently being received thereby, said third register receiving consecutively and storing temporarily therein said digitized samples transferred from said second register, and wherein said system further comprises first and second comparator means each for comparing values of said digitized samples provided thereto and providing signals at an output thereof indicating whether one of those digitized samples has a value which is greater than, less than or equal to that of that other one provided thereto, said first comparator means being connected to said first and second registers to receive representations of those said digitized samples currently being stored in each for comparison, said second comparator means being connected to said second and third registers to receive representations of those said digitized samples currently being stored in each for comparison, and wherein said signal processing means further comprises a logic means for determining whether signals provided thereto are identical or differ and of providing signals at an output thereof indicating which condition is currently occurring, said logic means being electrically connected to said outputs of each of said first and second comparator means, and wherein said signal processing means further contains a first shift register means for receiving current signal portions at an input thereof for temporary storage therein and shifting each such signal portion along storage sites therein as each successive current signal portion is received at said input with said first shift register means input being electrically connected to said logic means output, each of said storage sites having a storage site output to which it is connected.

19. The system of claim 10 wherein said signal processing means comprises a first, a second and a third register, each for storing a said digitized sample, said first register receiving consecutively and storing temporarily therein each said digitized sample provided by said analog-to-digital converter means and transferring to said second register for temporary storage therein that digitized sample immediately preceding each said digitized sample currently being received thereby, said second register receiving consecutively and storing temporarily therein said digitized samples transferred from said first register and transferring to said third register for temporary storage therein that digitized sample immediately preceding each said digitized sample currently being received thereby, said third register receiving consecutively and storing temporarily therein said digitized samples transferred from said second register, and wherein said system further comprises first and second comparator means each for comparing values of said digitized samples provided thereto and providing signals at an output thereof indicating whether one of those digitized samples has a value which is greater than, less than or equal to that of that other one provided thereto, said first comparator means being connected to said first and second registers to receive representations of those said digitized samples currently being stored in each for comparison, said second comparator means being connected to said second and third registers to receive representations of those said digitized samples currently being stored in each for comparison, and wherein said signal processing means further comprises a logic means for determining whether signals provided thereto are identical or differ and of providing signals at an output thereof indicating which condition is currently occurring, said logic means being electrically connected to said outputs of each of said first and second comparator means, and wherein said signal processing means further contains a first shift register means for receiving current signal portions at an input thereof for temporary storage therein and shifting each such signal portion along storage sites therein as each successive current signal portion is received at said input with said first shift register means input being electrically connected to said logic means output, each of said storage sites having a storage site output to which it is connected.

20. The system of claim 19 wherein said system further comprises a subsequence selector means connected to each of said storage site outputs and for receiving and storing temporarily said signal portions and making them available at least at one output thereof, and wherein said system further comprises an arithmetical combining means for performing arithmetic operations on signal portions provided thereto at at least one input thereof, said arithmetical combining means input being electrically connected to said subsequence selector means output.

* * * * *

UNITED STATES PATENT AND TRADEMARK OFFICE
CERTIFICATE OF CORRECTION

PATENT NO. : 4794533
DATED : December 27, 1988
INVENTOR(S) : Daniel E. Cohen

It is certified that error appears in the above-identified patent and that said Letters Patent is hereby corrected as shown below:

Column 12, Line 6, delete "if" and insert "is"

Column 13, Line 3, delete "subsequences" and insert "subsequence"

Signed and Sealed this

Second Day of May, 1989

Attest:

DONALD J. QUIGG

Attesting Officer

Commissioner of Patents and Trademarks